US011998420B2

(12) United States Patent
Hornbeck

(10) Patent No.: US 11,998,420 B2
(45) Date of Patent: Jun. 4, 2024

(54) SCREWDRIVER AND SCREW FOR A SURGICAL APPLICATION

(71) Applicant: JADE FINANCE S.A.R.L., Luxembourg (LU)

(72) Inventor: Jacques Hornbeck, Luxembourg (LU)

(73) Assignee: JADE FINANCE S.A.R.L., Luxembourg (LU)

( * ) Notice: Subject to any disclaimer, the term of this patent is extended or adjusted under 35 U.S.C. 154(b) by 914 days.

(21) Appl. No.: 16/461,156

(22) PCT Filed: Nov. 15, 2017

(86) PCT No.: PCT/EP2017/079296
§ 371 (c)(1),
(2) Date: May 15, 2019

(87) PCT Pub. No.: WO2018/091515
PCT Pub. Date: May 24, 2018

(65) Prior Publication Data
US 2019/0274793 A1    Sep. 12, 2019

(30) Foreign Application Priority Data

Nov. 15, 2016    (LU) .......................................... 93307

(51) Int. Cl.
*A61C 8/00* (2006.01)
*A61B 17/86* (2006.01)
*A61B 17/88* (2006.01)

(52) U.S. Cl.
CPC ........ *A61C 8/0089* (2013.01); *A61B 17/8615* (2013.01); *A61B 17/888* (2013.01); *A61B 17/8888* (2013.01); *A61C 8/0068* (2013.01)

(58) Field of Classification Search
CPC . A61C 8/0089; A61C 8/0068; A61B 17/8615; A61B 17/888; A61B 17/8888; F16C 11/0623
See application file for complete search history.

(56) References Cited

U.S. PATENT DOCUMENTS 8,096,212 B2 * 1/2012 Su ............................ B25G 3/38
81/177.85
9,763,754 B2    9/2017 Haus
(Continued)

FOREIGN PATENT DOCUMENTS

DE    202008016076 U1    2/2009
DE    202009009500 U1    11/2009
(Continued)

OTHER PUBLICATIONS

International Search Report issued Dec. 18, 2017 re: Application No. PCT/EP2017/079296, pp. 1-4.
(Continued)

*Primary Examiner* — Cris L. Rodriguez
*Assistant Examiner* — Drew S Folgmann
(74) *Attorney, Agent, or Firm* — CANTOR COLBURN LLP

(57) ABSTRACT

A system for fastening an orthopaedic implant either to a bone or to an orthopaedic implant, including a screw and a driver; the screwing having a first end and an apical end, a head at the first end and a thread at the apical end, a bore running axially from the first end of the screw along a portion of the screw towards the apical end of the screw, a first zone at the first end of the bore and a second zone at the apical end of the bore, where the first and second zones have clipping and peripheral engagement means, respectively, where the driver includes a head having first and second segments, the first segment having means for triggering the clipping means during an axial insertion of the driver head into the bore, where the second segment has means for engaging the peripheral engagement means, and where the second segment of the driver head has a rounded axial section, and the second zone of the bore has a rounded socket shape adapted to engage with the second segment of (Continued)

the driver head in various angled positions of the driver versus the axial direction of the screw.

15 Claims, 4 Drawing Sheets

(56) References Cited

U.S. PATENT DOCUMENTS

| | | |
|---|---|---|
| 2012/0103147 A1 | 5/2012 | Berga et al. |
| 2013/0230825 A1 | 9/2013 | Kenk et al. |
| 2014/0205970 A1* | 7/2014 | Courvoisier ......... A61C 8/0089 433/174 |
| 2015/0005080 A1* | 1/2015 | Chu .................... B25B 23/0014 464/157 |

FOREIGN PATENT DOCUMENTS

| | | |
|---|---|---|
| DE | 102009015358 A1 | 9/2010 |
| EP | 2420354 A1 | 2/2012 |
| EP | 2607722 A1 | 6/2013 |
| JP | 2010051708 A | 3/2010 |
| JP | 2014520578 A | 8/2014 |
| WO | 2013004386 A1 | 1/2013 |

OTHER PUBLICATIONS

Written Opinion Dec. 18, 2017 re: Application No. PCT/EP2017/079296, pp. 1-6.
JP Office Action issued Oct. 26, 2021 re: Application No. 2019-547183, pp. 1-8.
KR Office Action issued May 6, 2022 re: Application No. 10-2019-7017096, pp. 1-16.

* cited by examiner

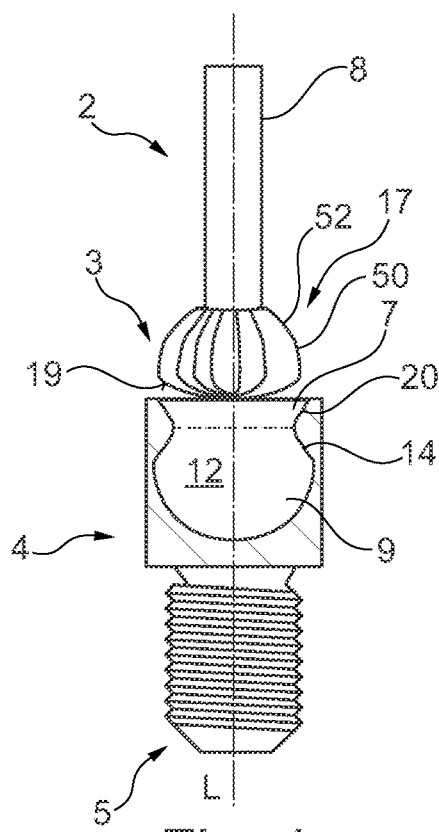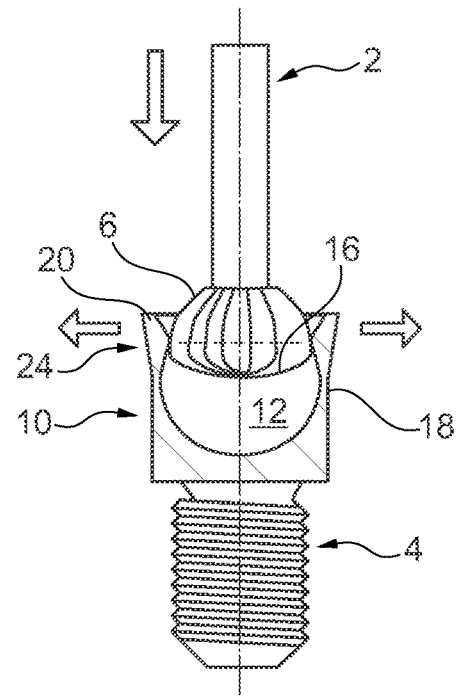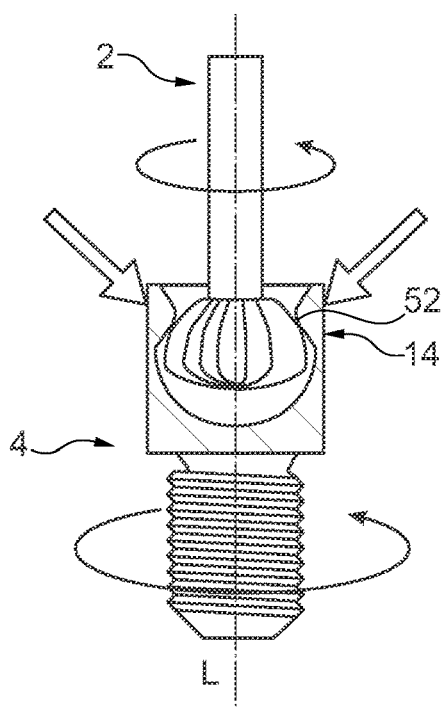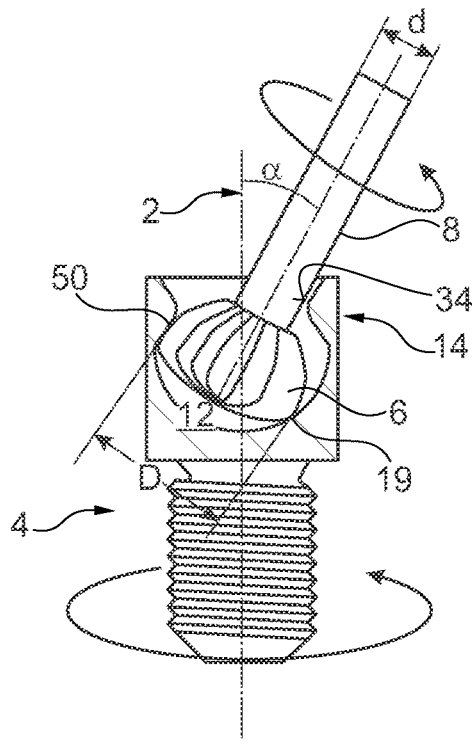

SCREWDRIVER AND SCREW FOR A SURGICAL APPLICATION

TECHNICAL FIELD

The present disclosure generally relates to the field of surgical implants and in particular for dental prostheses fixation. The disclosure relates to a combination of a screwdriver and a screw for fastening orthopaedic Implants either to bone or to an orthopaedic implant, in particular to a dental component to a dental implant fixing dental implant fixation. It also relates to a process of operation of the combination.

BACKGROUND

It is known to use screws to fix an artificial denture to an implant in the jaw-bone. The artificial dentures generally comprise a tooth crown or a bridge with two or more artificial teeth, where the tooth crown or the bridge is connected to the dental implant by one or more screws. A screwdriver is used to screw or unscrew such a screw in the implant. There is a risk however that the screw while manoeuvring in the mouth of the patient falls into the mouth of the patient and be swallowed or breathed in.

WO 2013/004386 A1 discloses a combination of a screw for a dental application and a driver for driving the screw for fastening a dental component to a dental implant, the screw having a coronal end and an apical end and comprising: a bore running from the coronal end of the screw along a portion of the screw towards the apical end of the screw, a first number of equally spaced recesses arranged circumferentially around an inside surface of the bore, each recess running a length from the coronal end of the bore towards the apical end of the bore and being connected to flat engagement surfaces. The recesses and the engagement surfaces are angled relative to the axial direction of the screw so that they form a bore with a section that is reducing with an increasing distance to the coronal end of the bore.

The driver comprises a driver head which presents a polygonal transversal section able to engage with the engagement surfaces of the bore. The driver head comprises a first portion at distance from the tip of the driver head that has a rounded cross section configured to engage with the engagement surface for the couple transmission on the screw. The pressure exercised by the driver in the bore creates a friction between the first portion of the driver head and the engagement surfaces in the bore, so that the screw can be held by the driver head. The solution is interesting because the combination allows a carry function of the screw; it also allows a couple transmission operation with an inclination of the driver with regard to the axial direction of the screw. However, the carry function is not very effective as a slight change of angular orientation of the driver head in the bore may release the screw. Furthermore the carry function may weaken over time/use since the friction forces may diminish when the screw is set on the screwdriver repeatedly.

DE 10 2009 015358 A1 discloses a screw comprising a screw head and a screw shaft, wherein the screw shaft comprises a chamber for receiving a wrench. The chamber is conical and comprises a plurality of first guiding surfaces as well as a plurality of second guiding surfaces, which are undercut with respect to the first guiding surfaces. These guiding surfaces correspond to guiding surfaces of the wrench. Between the first and second guiding surfaces, there are force transfer surfaces for cooperating with corresponding force transfer surfaces of the wrench.

DE 20 2009 009500 U1 discloses a screw profile for use in connection with dental implants. The profile comprises a screw head with a chamber for receiving a tool head of an assembly tool, and a screw shaft. Within the chamber, there is a groove or a ridge for cooperating with a corresponding ridge or groove of the tool head in order to latchingly connect the screw head with the assembly tool. The only embodiment shows a hexagon socket head screw and a corresponding hexagon socket head wrench.

EP 2 420 354 A1 discloses a coupling tool for use with a screw head. The tool comprises a rod having at one end a truncated cone-like surface and a protuberance having at one end a base portion located adjacent said surface and at the other end a pole. The protuberance has a plurality of meridional grooves having a curved concave transverse section, separated from one another by spherical lunes having a curved convex external surface. The screw head has a recess and axial projections which cooperate with the meridional grooves.

BRIEF SUMMARY

The present disclosure provides a solution which overcomes the disadvantages of the prior art, in particular of the prior art cited above. More particularly, the present disclosure provides a solution of a combination of a driver and a screw that improves the carry function of the screw by the driver.

According to the present disclosure, a combination of a screw for a surgical application, and a driver for driving the screw for fastening orthopaedic Implants either to bone or to an orthopaedic implant in particular a dental component to a dental implant is proposed, the screw having a first end and an apical end, a head at its first end and a thread at its apical end, a bore running axially from the first end of the screw along a portion of the screw towards the apical end of the screw, a first zone at the first end of the bore and a second zone at the apical end of the bore, the first zone of the bore comprises clipping means and the second zone of the bore comprises peripheral engagement means; the driver comprises a driver head having a first and a second segment, the first segment comprises means for triggering the clipping means in the first zone of the bore during the axial insertion of the driver head into the bore so as to maintain the screw releasably fastened to the driver; the second segment comprises means for engaging the peripheral engagement means in the second zone at the apical end of the bore for the transmission of a couple to fasten or loosen the screw; the second segment of the driver head has a substantially rounded axial section, and the second zone of the bore has a rounded socket shape adapted to engage with the second segment of the driver head in various angled positions of the driver versus the axial direction of the screw.

The merit of the disclosure is to provide a solution where the screw is safely and temporarily fastened/secured to the driver so that the dentist can manoeuvre the screw fastened on the screwdriver inside the mouth of the patient without risking losing the screw. The fastening mechanism works reliably when the screw is to be fixed on the dental implant but also when the screw is to be removed from the dental implant. Indeed, the clipping means in the first zone of the bore allow the screw to be securely held by the first segment of the driver head. The second segment of the driver head engages with the engagement means of the bore that are situated in the second zone of the bore for couple transmission i.e. to screw or unscrew the screw into or out of the implant.

The clipping means not only allow to securely holding/maintaining/retaining the screw on the tip of the screwdriver but they also give a feedback to the operator that the screw is firmly engaged/secured/clipped on the screwdriver. The operator can indeed feel and/or hear when the clipping means is triggered. It takes a certain force to trigger the clipping means, to overcome the resistance since the clipping means are "pushed aside" when the head of the screwdriver engages the bore of the screw. The clipping means snap back in their original position after the head of the screwdriver is inserted in the bore and thus maintains the screw on the driver head. The clipping means thus involve an elastic deformation of the walls surrounding the bore of the screw. This force is such that the screw can easily be pushed onto the driver by two fingers and can also be released by excreting a pull on the screwdriver by to fingers. This force is estimated at about 2 Newton+/0.5 Newton.

There may be a gap between the driver head and the second zone in the bore so that the driver head is not jammed/stuck in the second zone of the bore while the screw is secured in position on the driver head. This allows changing the orientation of the driver, i.e. to tilt the driver relative to the axis of the screw when rotating the screw for couple transmission.

The poor holding performance of the screw disclosed in WO 2013/004386 A1 is due to the fact that the screw is fastened to the driver only through friction forces, which are created by the fact that the engagement means are angled relative to the axial direction of the screw so as to form a bore with a tapered section i.e. that is reducing with an increasing distance to the first end of the bore. The engagement means of the bore are used as friction surfaces to maintain the screw on the screwdriver. This is however unreliable since the friction forces may be different when the screw/screwdriver are wet or dry. The friction forces differ also with each screw or with each screw/screwdriver combination. Finally the user gets no feedback as to when the screw is securely fastened to the screwdriver. Furthermore, when repeatedly used, the friction forces may diminish.

In a preferred embodiment, the clipping means are regularly spaced around the circumference of the first zone of the bore.

Advantageously, the head of the screw has an external profile which is circular. The external diameter of the head of the screw can be between 1.5 mm and 3 mm.

In a preferred embodiment, the engagement means can form a mutlilobular transversal profile, preferably a pentalobular profile. Alternatively, the engagement means can form a Torx™ profile. The engagement means are thus not angled relative to the axial direction of the screw as in in WO 2013/004386 A1.

The head comprises a peripheral wall around the bore. In a preferred embodiment, the clipping means comprise a portion of the peripheral wall that is able to be deformed radially and elastically. When the screwdriver head is inserted into the bore of the screw, the clipping portion is pushed outward due to the outwardly radially oriented forces and the clipping means pivot radially outwardly and to clip back-in, by a spring effect, by pivoting radially inwardly. At the pivot zone, the minimum thickness of the peripheral wall is between 0.1 mm and 0.5 mm.

The peripheral wall at the level of the clipping means has a thickness of less than 0.1 mm.

The peripheral wall at the level of the clipping means has a thickness of more than 0.5 mm so as to guarantee a minimal stability of the screw head.

In a preferred embodiment, the pivot zone extends around the entire circumference of the bore and is preferably situated at about half of the depth of the bore. The depth of the bore can be between 0.8 mm and 1.5 mm.

As mentioned above, the second segment of the driver head has a substantially rounded axial section, and the second zone of the bore has a rounded socket shape adapted to cooperate with the second segment of the driver head in various angled positions of the driver with regard to the length of the screw—i.e. from the first end to the apical end of the screw.

In a preferred embodiment, the second segment has a diameter that is reducing with the increasing distance to the tip of the screwdriver. It presents a first and second linear or curved sub-portion, proximal and distal to the tip of the driver, respectively. The peripheral engagement means are arranged in the second zone of the bore so as to cooperate with the second, distal, linear or curved sub-portion and the first, proximal, linear or curved sub-portion, when the driver is in the axial direction and is angled versus the axial direction, respectively.

In a preferred embodiment, the curved sub-portions are curved with opposite convexities and present an axial profile with a form of an "S".

In a preferred embodiment, the second zone at the apical end of the bore comprises a spherical surface extending from the apical end of the bore to the peripheral engagement means, the first segment of the driver head comprising a peripheral surface able to abut against said spherical surface when the driver head is inserted in the screw and is in the axial direction or angled relative to the axial direction. Advantageously, the first segment of the driver head extends substantially transversally.

In a preferred embodiment, the clipping means comprise clipping protrusions which are preferably uniformly spaced around the periphery of the bore. The clipping protrusions may comprise radially inwardly oriented apices forming a circumferential interface apice line between the first zone and the second zone of the bore. The ratio between the diameter formed by the circumferential interface apice line and the diameter of the external profile of the head of the screw is between 0.6 and 0.8. The minimum diameter is preferably 1.3 mm and the maximum diameter is preferably 1.75 mm.

In a preferred embodiment, the clipping protrusions comprise a contact surface starting from the apices and extending radially outwardly towards the first end of the bore.

In a preferred embodiment, this contact surface is a conical surface around the axis of the screw at the mouth of the bore i.e. the first end of the screw.

In a preferred embodiment, the clipping protrusions comprise securing surfaces starting from the apices and extending radially outwardly towards the apical end of the bore, the second segment of the driver head forming a generally outwardly curved axial profile toward the tip of the driver configured to abut said securing surfaces.

In a preferred embodiment, the contact surfaces and/or the securing surfaces are inclined with regard to the axial direction i.e. the length of the screw with an angle between 10° and 80°, preferably between 20° and 40°.

In a preferred embodiment, the peripheral engagement means comprise a peripheral engagement surface in the second zone of the bore forming a multilobular transversal profile, preferably a pentalobular profile, the protruding zones of the multilobular profile comprising the securing surfaces of the clipping protrusions. Advantageously, the ratio between the radius of the apices of the protruding zone of the engagement profile and the radius of the recesses of the engagement profile is between 0.6 and 0.8.

In a preferred embodiment, the screw is made of Titanium alloy.

In a preferred embodiment, the driver comprises a shaft linked to the driver head and the shaft has a diameter that is between 40% and 50% of the maximum diameter of the driver head.

The disclosure also relates to a process of operation of a combination of a driver with a screw, comprising the steps:
a) alignment of the driver with the axial direction of the screw;
b) contact of the first zone of the driver head with the clipping means of the screw;
c) axial pressure exercised by the first segment of the driver head on the clipping means for triggering the clipping mechanism of said clipping means;
d) axial penetration of the driver head from the first zone to the second zone of the bore;
e) rotation of the driver for engaging the second segment of the driver head with the peripheral engagement means in the bore for couple transmission.

Alternatively to step e), the driver can be inclined of by an angle (a) from the axial direction of the screw and the driver can be rotated for engaging the second segment of the driver with the peripheral engagement means in the bore for couple transmission.

Advantageously, the ratio between the length in the axial direction of the head at the first end of the screw and the length of the thread at the apical end of the screw is between 0.8 and 2.

BRIEF DESCRIPTION OF THE DRAWINGS

FIG. 4 is an illustration of a first step of a process of operation of the combination of FIGS. 1A and 1B;

FIG. 5 is an illustration of intermediate steps of a process of operation of the combination of FIGS. 1A and 1B;

FIG. 6 is an illustration of a final step of a process of operation of a combination of FIGS. 1A and 1B;

FIG. 7 is an illustration of an alternative final step of a process of operation of a combination of FIGS. 1A and 1B;

DETAILED DESCRIPTION OF PREFERRED EMBODIMENTS

Figures 1A, 1B:
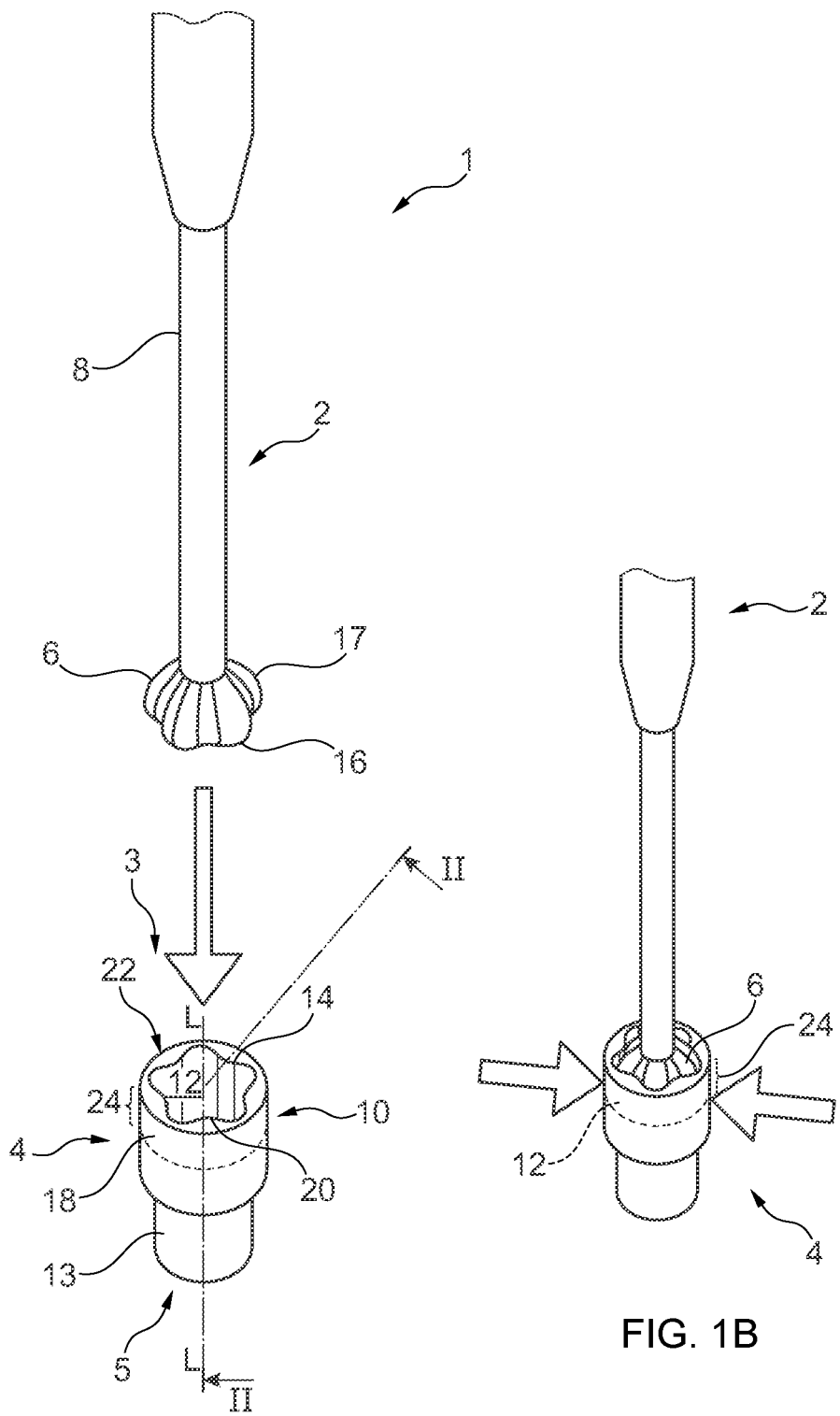
FIGS. 1A and 1B are schematic views of a preferred embodiment of a combination of a screwdriver and a screw according to the disclosure.

FIGS. 1A and 1B are a view of a combination 1 of a driver 2 and a screw 4 for a dental application according to a preferred embodiment to the disclosure. The screw 4 is intended to be used for dental prosthesis fixation, for example for fixing a tooth crown on an implant. The screw 4 has a coronal end 3 and an apical end 5, a head 10 at the coronal end 3 and a thread 13 at the apical end 5. The head comprises a bore 12 running axially from the coronal end 3 of the screw 4 along a portion of the screw towards the apical end 5 of the screw.

On FIG. 4, it can be seen that the bore 12 comprises a first zone 7 towards the coronal end 3 of the screw 4 and a second zone 9 at the apical end of the bore (towards the apical end 5 of the screw 4). The first zone 7 at the coronal end of the bore 12 comprises clipping means 20 and the second zone 9 of the bore 12 comprises peripheral engagement means 14.

The driver 2 comprises a driver head 6 with a first 16 segment and a second 17 segment. The first segment 16 comprises means 19 (see FIG. 4) for triggering the clipping means 20 in the first zone 7 at the coronal end of the bore during the axial penetration of the driver head 6 into the bore. These clipping means so maintain the screw releasably fastened to the driver.

The second segment 17 of the driver head 6 comprises means for engaging the peripheral engagement means 14 in the second zone 9 at the apical end of the bore 12 for the couple transmission. FIG. 1A illustrates the driver 2 positioned outside of the screw 4. The shaft 8 of the driver 2 is positioned in an alignment with the longitudinal axis L of the screw. The driver head 6 comprises a profile on its second segment 17 which is configured to cooperate with the engagement means 14 of the screw 4.

The driver head 6 of the driver 2 presents a substantially ball shaped axial profile. The driver head 6 presents a first segment 16 which is extending substantially transversally.

The peripheral engagement means 14 on the screw 4 comprise a peripheral surface (only partially visible) in the second zone 9 of the bore 12 and forms a multilobular transversal profile. The engagement surface forms a pentalobular profile.

The clipping means 20 are regularly spaced on the circumference of the bore. The clipping means comprise clipping protrusions 26 uniformly spaced on the periphery of the bore 12. The head 10 of the screw 4 comprises a peripheral wall 18 around the bore 12 and the clipping means 20 comprise a clipping portion 24 of the peripheral wall 18 that is able to deform radially and elastically. FIG. 1B illustrates the driver head 6 of the driver 2 positioned inside the bore 12 of the screw 4 beyond the clipping means 20. The clipping portion 24 of the peripheral wall 18 is subjected to a radial and elastical deformation when the screwdriver is pushed in the bore and the clipping means snap back in their original position once the driver head is inserted in its final position in the second zone of the bore of the screw. The driver head 6 of the driver is thus secured inside the bore 12 after the introduction of the driver head 6 in the bore. This is possible thanks to the spring effect of the clipping portion 24 when deformed back radially inwardly.

Figure 2:
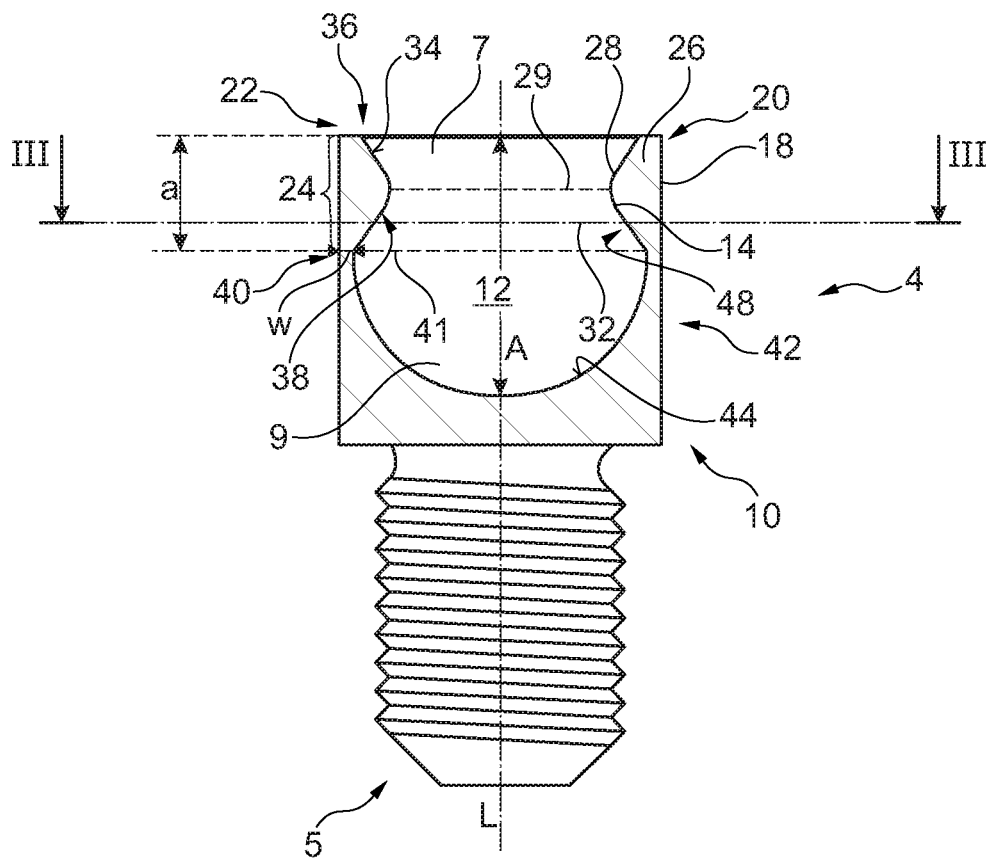
FIG. 2 is an axial cross section II-II of the screw of the combination of FIGS. 1A and 1B.

FIG. 2 is an axial section II-II of the screw 4, with the peripheral wall 18 of the head 10 around the bore 12 of the screw, the clipping portion 24 of the peripheral wall, the clipping means 20 situated in the first zone 7 at the coronal end of the bore as well as the clipping protrusions 26 in the bore. The clipping protrusions 26 are protruding into the bore and are uniformly spaced on the periphery of the bore. The clipping protrusions 26 present inwardly radially oriented apices 28 that form a circumferential interface apices line. The clipping protrusions 26 comprise contact surfaces 34 which are starting from the apices 28 and extending radially outwardly towards the coronal end of the bore 12. The contact surfaces 34 are intended to be pressed in the axial direction of the screw by the first segment of the driver head so that the clipping portion 24 of the peripheral wall 18 is deformed radially outwardly.

The edge 36 of the peripheral wall 18 at the coronal end of the bore 12 forms a conical surface that incorporates the contact surfaces 34.

The clipping protrusions 26 further comprise securing surfaces 38 starting from the apices 28 and extending radially outwardly towards the apical end of the bore 12. The contact surfaces 34 and/or the securing surfaces 38 are generally inclined with regard to the axial direction of the screw with an angle between 10° and 80°. Preferably, the contact and engagement surfaces can be inclined with an angle between 20° and 40°.

The ratio between the diameter formed by the circumferential interface apices line and the maximum diameter in the second zone 9 of the screw 4 may be up to 0.99, it is preferably between 0.7 and 0.9.

The contact surfaces 34 are designed for a predetermined insertion force, preferably with two fingers. This force is estimated at about 2 Newton+/0.5 Newton.

The securing surfaces 38 are designed so that the retention force on the screw 4 by the driver head 6 is above a minimum force corresponding to a multiple of the weight of the screw 4, preferably above 10 times its weight, more preferably above 20 times its weight.

The ratio between the predetermined insertion force and the retention force is between 0.5 and 2.5, preferably between 0.9 and 1.1. The peripheral wall 18 undergoes a peripheral deformation location 40 and is constructed to pivot while the clipping means are triggered.

In the present embodiment, the deformation is extending in the circumference of the peripheral wall 18 and presents a minimum width "w" in the peripheral wall. That peripheral deformation location 40 is at a distance "a" of the coronal end of the bore 12. The clipping portion 24 is able to pivot radially.

In the present embodiment, the clipping portion is situated at a distance of the coronal end of the head of the screw between 20% and 60% of the depth of the bore.

The engagement means 14 are situated in the second zone 9 of the bore 12. A rounded bottom axial profile 42 is shown extending from the apical end of the bore 12 in the direction to the coronal end of the bore up to the engagement means 14 in the second zone 9. The rounded axial profile 42 forms curved engagement surfaces 44 in the second zone.

At the apical end 5 of the screw 4, there is a threaded part of the screw and a shoulder on the bottom of the head 10 of the screw. The type of thread and the form of the shoulder illustrated do not limit the scope of the disclosure.

Figure 3:
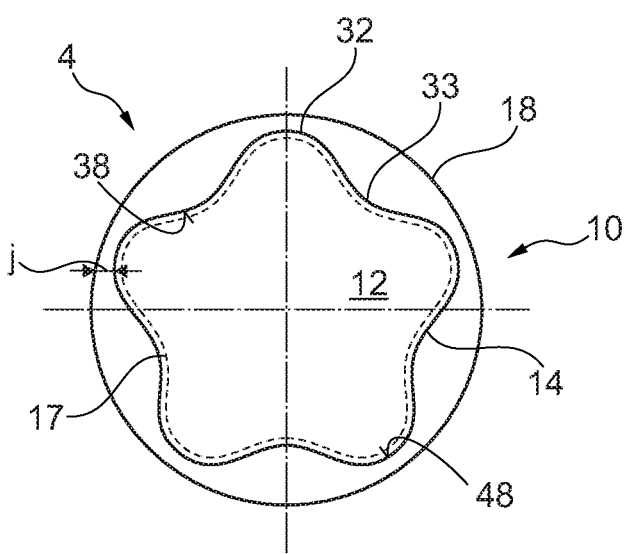
FIG. 3 is a transversal cross section of the screw of the combination of FIGS. 1A and 1B.

FIG. 3 shows a transversal section of the screw 4 of FIGS. 1A and 1B. The pentalobular profile of the peripheral surface forming the engagement means 14 can be seen. The protruding zones of the pentalobular profile are formed by the engagement protrusions 33 of the engagement means 14 that comprise the securing surfaces 38. It is interesting to note on this view the dashed line representing the engagement surface of the second segment 17 of the driver head 6, able to engage with the engagement means 14 of the screw for couple transmission, that present a gap with the engagement surface in the bore 12. In relation with FIGS. 6 and 7, it is shown that the first segment 16 of the driver head 6 is configured to abut at the apical end of the bore 12, therefore the gap between the second segment 17 of the driver head and the engagement means 14 allows an easy orientation of the driver around the axis of the screw before or while rotating the driver. The engagement means 14 further comprise engagement recesses 32 which are situated between the protruding surfaces in the bore. The engagement recesses are extending along the longitudinal axis L of the screw 4 and are not tapered.

The engagement means 14 extending on the engagement protrusions 33 and engagement recesses 32 are designed in order to allow the transmission of a couple with no deformation of the second zone, at least in comparison with the deformation of the screw during the driver head insertion. Preferably, the ratio between the engagement surfaces in the second zone 9 and the contact surfaces 34 in the first zone (see FIG. 2) is between 5 and 15.

FIG. 4 is an illustration of the first step of a process of operation of the combination. In this first step, the shaft 8 of the driver 2 is aligned with the axial direction of the screw 4. It can be observed that the second segment 17 of the driver head 6 has a substantially rounded axial section and that the second zone 9 of the bore 12 has a rounded socket shape adapted to cooperate with the second segment 17 of the driver in various angled orientations of the driver with regard to the axial direction of the screw (see also FIG. 7). FIG. 4 shows that the second segment 17 of the driver head 6 has a diameter in the transversal direction that is decreasing with the increasing distance to the tip of the driver. In particular, the second segment 17 of the driver head 6 comprises a first 50 and a second 52 linear sub-portion. The first linear sub-portion 50 is proximal to the tip and the second linear sub-portion 52 is distal to the tip.

The peripheral engagement means are arranged in the second zone 9 of the bore, close to the interface with the first zone, in order to cooperate with the second, linear sub-portion 52 (see also FIG. 6). Finally it is shown that the peripheral engagement means 14 are arranged in the second zone of the bore, close to the interface with the first zone, in order to cooperate with the first, linear sub-portion 52 when the driver is in an angled position with regard to the direction of the screw (see also FIG. 7).

FIG. 5 is an illustration of the steps b) to d) of the process:
b) contact of the first section 16 of the driver head 6 with the clipping means 20 of the screw;
c) axial pressure exercised by the first segment 16 of the driver on the clipping means 20 so as to spread them "out of the way" for triggering the clipping mechanism of said clipping means 20; and
d) axial penetration of the driver head from the first zone 7 to the second zone 9 of the bore 12 and snapping back of the clipping means in their original position.

FIG. 6 is an illustration of the final step e) of the process. The step e) comprises the rotation of the driver 2 and the engaging of the second segment 17 of the driver with the peripheral engagement means 14 in the bore for couple transmission. In the orientation of the driver as shown in FIG. 6, the distal end to the tip sub-portion 52 of the second segment 17, the one with a smaller diameter compared to the proximal sub-portion 50, engages with the engagement means 14 of the screw. In this axial orientation of the driver, the first segment 16 of the driver head 6 abuts against the curved surface 44 at the apical end of the bore while a gap (not visible) is present between the second segment 17 of the driver head and the engagement means 14 of the screw to prevent arc-boutement of the driver head.

In FIG. 7 the driver is inclined by an angle (a) from the axial direction of the screw 4 and the rotation of the driver 2 engages the second segment 17 of the driver with the peripheral engagement means 14 in the bore for couple transmission. During the rotation, the driver head 6 is secured in the bore 12 and the shaft 8, which is extending out of the bore 6, is "rolling" on the conical contact surface 34. In particular, the shaft 8 is inclined with an angle "a" which is between 20° and 30° relative to the longitudinal axis L. In this angled orientation tip sub-portion 50 of the second segment 17, the one with a larger diameter compared to the distal sub-portion 52 that engages with the engagement means 14 of the screw. In this angled orientation of the driver, the first segment 16 of the driver head 6 abuts against the spherical surface of the bore while a gap (not visible) is present between the second segment 17 of the driver head and the engagement means 14 of the screw to prevent arc-boutement of the driver head.

The gap (not visible) mentioned in relation with FIGS. 6 and 7 between the second segment 17 of the driver head 6 and the engagement means 14 may be positioned with an angle on the periphery of the second zone 9.

The abutment between the first segment 16 (see FIG. 6) or second segment (see FIG. 7) of the driver head 6 and the spherical or curved surface 44 of the second zone 9 may happen on a position on the driver head, situated at the interface between the first and second segments, that presents the larger external diameter.

Figure 8:
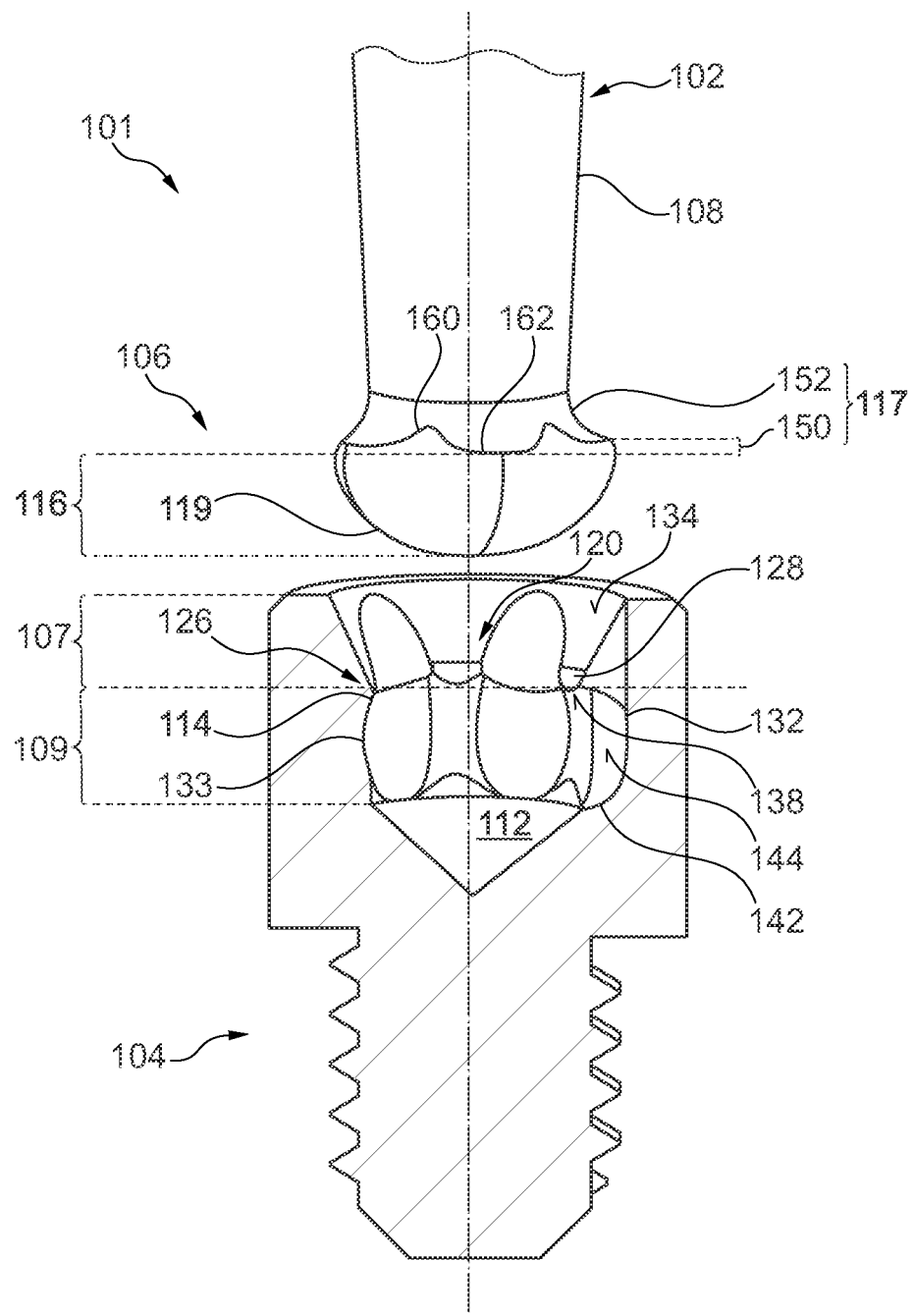

FIG. 8 is a view of a further preferred embodiment of a combination of a screwdriver 102 and a screw 104 according to the disclosure.

The screwdriver 102 comprises the driver shaft 108 and the driver head 106. The driver head 106 comprises a first and a second segment 116 and 117.

The first segment 116 comprises the triggering surfaces 119 for triggering the clipping means 120 on the screw 102. In this embodiment, the axial profile of the first segment 116 is ball-shaped with an external diameter that increases with the distance to the tip of the driver. The radial profile of the first segment 116 is pentalobular.

The second segment 117 of the driver is distal to the tip of the driver head 106 in comparison with the first segment 116. The axial profile of the second segment 117 forms an "S" shape with an external diameter. It decreases with the distance to the tip of the driver. The second segment presents sub-portions 150 and 152 that are curved with opposite convexities. The first sub-portion 150 presents a convex shape and the second sub-portion 152 presents a concave shape. The radial profile of the second segment 117 is pentalobular. The form of the driver head recesses 160 and of the driver head protrusions 162 in the second zone 117 due to the pentalobular profile is shown.

The screw 104 has a bore 112 with a first zone 107 at the coronal end of the bore and a second zone 109 at the apical end of the bore with the clipping means 120 situated in the first zone 107 and the engagement means 114 situated in the second zone.

The surfaces 134 form a conical shape in the first zone 107 of the bore and are adapted to enter in contact with the first segment 116 of the driver head 106 during insertion. The apices 128 of the clipping protrusions 126 at the interface of the first and the second zone 107 and 109 of the bore 112 are shown. The securing surfaces 138 in the second zone 109 are adapted to retain the second segment 117 of the driver head 106 after the driver head 106 has been inserted in the screw.

In the second zone 109, the pentalobular radial profile of the bore 112 forms regularly spaced engagement recesses 132 and engagement protrusions 133 of the engagement means 114. The rounded axial profile 142 of the second zone 109 forms curved engagement surfaces 144. In this case the bore is terminated at the apical end with a conical form beyond the second zone 109.

Although the above figures describe the disclosure in relation to a dental prosthesis fixation, it is clear to those skilled in the art that the screw and screwdriver can be used with any other orthopaedic implant for fastening orthopaedic Implants either to a bone or to an orthopaedic implant.

The invention claimed is:

1. A system for fastening an orthopaedic implant either to a bone or to another orthopaedic implant, the system comprising:
a screw; and
a driver;
wherein the screw comprises:
a first end and an apical end, a head at the first end and a thread at the apical end,
a bore running axially from the first end of the screw along a portion of the screw towards the apical end of the screw,
a first zone at the first end of the bore and a second zone at the apical end of the bore,
clipping means comprising clipping protrusions with a contact surface and a securing surface,
wherein the first zone of the bore comprises the contact surfaces of the clipping means and the second zone of the bore comprises peripheral engagement means,
wherein the driver comprises:
a driver head having a first and a second segment,
wherein the first segment comprises means for triggering the clipping means in the first zone of the bore during an axial insertion of the driver head into the bore so as to maintain the screw releasably fastened to the driver,
wherein the second segment comprises means for engaging the peripheral engagement means in the second zone at the apical end of the bore for transmission of a couple to fasten or loosen the screw,
wherein the second segment of the driver head has a substantially rounded axial section, and the second zone of the bore has a rounded socket shape adapted to engage with the second segment of the driver head in various angled positions of the driver versus the axial direction of the screw; and
wherein the peripheral engagement means comprise a peripheral engagement surface in the second zone of the bore forming a multilobular transversal profile, protruding zones of the multilobular profile comprising the securing surfaces of the clipping protrusions.

2. The system according to claim 1, wherein there is a gap between the driver head and the bore in the second zone.

3. The system according to claim 1, wherein the clipping means is regularly spaced on the circumference of the first zone of the bore.

4. The system according to claim 1, wherein the screw head comprises a peripheral wall around the bore, the clipping means comprising a clipping portion on the peripheral wall that is able to deform radially and elastically.

5. The system according to claim 1, wherein the head comprises a peripheral wall around the bore, the clipping means comprising a clipping portion of the peripheral wall that extends in the axial direction from the first end of the head until one deformation point, the clipping portion being able to clip-out with outwardly radially oriented forces and to clip back-in, by spring effect.

6. The system according to claim 1, wherein the second segment of the driver head has a diameter that reduces with the increasing distance to the tip, and presents a first linear or curved sub-portion proximal to the tip of the driver and a second linear or curved sub-portion distal to the tip of the driver, the peripheral engagement means being arranged in the second zone of the bore in order to cooperate with the second linear or curved sub-portion when the driver is in the axial direction and the first linear or curved sub-portion, when the driver is angled versus the axial direction.

7. The system according to claim 6, wherein the curved sub-portions are curved with opposite convexities and present an axial profile with a form of an "S".

8. The system according to claim 6, wherein the second zone comprises a spherical surface extending from the apical end of the bore until the peripheral engagement means, the first segment of the driver head comprising a peripheral surface able to abut against said spherical surface when the driver is in the axial direction or angled versus the axial direction.

9. The system according to claim 1, wherein the clipping protrusions are uniformly spaced in the periphery of the bore with inwardly radially oriented apices forming a circumferential interface between the first zone and the second zone of the bore.

10. The system according to claim 9, wherein the contact surfaces start from the apices and extend radially outwardly towards the first end of the bore, the contact surfaces being intended to be pressed in the axial direction by the first segment of the driver head at introduction of the driver in order to bend radially and outwardly.

11. The system according to claim 10, wherein the first zone of the bore forms a conical surface around the axis of the screw, and comprises the contact surfaces.

12. The system according to claim 9, wherein the securing surfaces start from the apices and extend radially outwardly towards the apical end of the bore, the second segment of the driver head forming a generally outwardly curved axial profile toward the tip of the driver configured to abut said securing surfaces.

13. The system according to claim 10, wherein the contact surfaces and/or the securing surfaces are inclined with regard to the axial direction of the screw in an angle between 10° and 80°.

14. The system according to claim 1, wherein the screw is made of Titanium alloy.

15. The system according to claim 1, wherein the driver comprises a shaft linked to the driver head and the shaft has a diameter that is between 40% and 50% of the maximum diameter of the driver head.

* * * * *